(12) United States Patent
Nagaraja Rao et al.

(10) Patent No.: US 7,783,090 B2
(45) Date of Patent: Aug. 24, 2010

(54) AUTOMATIC IDENTIFICATION OF THE ANTERIOR AND POSTERIOR COMMISSURE LANDMARKS

(75) Inventors: Bhanu Prakash Kirgaval Nagaraja Rao, Singapore (SG); Wieslaw Lucjan Nowinski, Singapore (SG)

(73) Assignee: Agency for Science, Technology and Research, Centros (SG)

( * ) Notice: Subject to any disclaimer, the term of this patent is extended or adjusted under 35 U.S.C. 154(b) by 655 days.

(21) Appl. No.: 10/580,118

(22) PCT Filed: Nov. 1, 2004

(86) PCT No.: PCT/SG2004/000361

§ 371 (c)(1),
(2), (4) Date: May 19, 2006

(87) PCT Pub. No.: WO2005/048844

PCT Pub. Date: Jun. 2, 2005

(65) Prior Publication Data

US 2007/0076927 A1    Apr. 5, 2007

(30) Foreign Application Priority Data

Nov. 19, 2003   (SG) ............................ 200306861-6

(51) Int. Cl.
*G06K 9/00*    (2006.01)

(52) U.S. Cl. .................. 382/128; 382/133; 382/171; 382/293; 382/131; 382/132; 382/190; 382/286; 382/272; 600/407; 600/409; 600/410

(58) Field of Classification Search ................ 382/128, 382/171, 293, 115, 118, 131, 132, 133, 190; 600/407; 378/21
See application file for complete search history.

(56) References Cited

U.S. PATENT DOCUMENTS

| | | | |
|---|---|---|---|
| 5,262,945 A | 11/1993 | DeCarli et al. | |
| 6,178,271 B1 * | 1/2001 | Maas, III | 382/294 |
| 6,240,308 B1 * | 5/2001 | Hardy et al. | 600/407 |
| 6,466,687 B1 * | 10/2002 | Uppaluri et al. | 382/128 |
| 6,584,216 B1 * | 6/2003 | Nyul et al. | 382/131 |
| 7,340,099 B2 * | 3/2008 | Zhang | 382/191 |
| 7,646,898 B1 * | 1/2010 | Nowinski et al. | 382/128 |
| 2003/0009098 A1 * | 1/2003 | Jack et al. | 600/410 |
| 2003/0210820 A1 | 11/2003 | Lachner et al. | |

FOREIGN PATENT DOCUMENTS

| | | |
|---|---|---|
| JP | 2000-126150 | 5/2000 |
| WO | WO 02/43003 A1 | 5/2002 |

OTHER PUBLICATIONS

Fully Automatic Identification of AC and PC Landmarks on Brain MRI Using Scene Analysis Laurent V'erard, Pascal Allain, Jean Marcel Trav'ere, Jean Claude Baron, and Daniel Bloyet, 1997.*
Sun et al. "Anatomic Labelling of PET Brain Images with Automatic Detection of AC and PC", Journal of Digital Imaging, vol. 11(3 Supp.), pp. 56-58, Aug. 1998.
Arndt et al., "Landmark-based Registration and Measurement of Magnetic Resonance Images: A Reliability Study", Psychiatry Research: Neuroimaging, vol. 67(2), pp. 145-154, Jul. 1996.
Han et al., "Automatic Registration of Brain Magnetic Resonance Images Based on Talairach Reference System", Journal Magnetic Resonance Imaging, vol. 20(4), pp. 572-80, Oct. 2004.

* cited by examiner

*Primary Examiner*—Wes Tucker
*Assistant Examiner*—Nancy Bitar
(74) *Attorney, Agent, or Firm*—Dickstein Shapiro LLP (57) ABSTRACT

The AC and/or PC landmarks are identified in a midsagittal MRI image by firstly identifying structures in the brain (specifically the fornix and/or brainstem) as groups of pixels in a radiological image which have an intensity in ranges defined by one or more thresholds and which obey predefined geometrical criteria. The thresholds are varied until the predefined geometrical criteria are met. Initial estimates of the position of the AC and/or PC are derived from the identified structures. These estimates can be improved in various ways, especially by making use of axial and/or corona/radiological images in planes including, and/or proximate to, the initial estimated position of the AC and/or PC.

9 Claims, 12 Drawing Sheets

AUTOMATIC IDENTIFICATION OF THE ANTERIOR AND POSTERIOR COMMISSURE LANDMARKS

FIELD OF THE INVENTION

The present invention is related to methods and apparatus for identifying anterior commissure (AC) and/or posterior commissure (PC) landmarks from an image of a portion of a brain.

BACKGROUND OF INVENTION

Identification of the AC and PC are critical for operations such as targeting stereotactic and functional neurosurgery, localisation, analysis in human brain mapping, structure segmentation and labelling in neuroradiology. The Talairach atlas has been widely used as a common standard by neuroscientists and neurosurgeons. To perform spatial normalisation using either standard or modified Talairach transformations, the MSP (midsagittal plane), AC and PC have to be identified.

Currently experts perform the detection of these structures manually. However, observer reproducibility is less accurate and prohibitively time-consuming when large sets of data have to be analysed. Furthermore, there is a certain degree of variability among different experts in tracing these landmarks. For these reasons, there is a need to automate the process of identification with accurate, robust and efficient algorithms.

Sun Y. H. et al, in the article "Anatomic labelling of PET brain images with automatic detection of AC and PC", J. Digit Imaging, 1998 August; 11 (3 Suppl 1):56-58, describe an automatic detection method for finding the AC and PC from positron emission tomography (PET) brain images. However, the resolution of PET images is very low, and the AC and PC are particularly difficult to identify in such images. Thus, the algorithm is only able to identify the AC and PC with a high level of uncertainty.

Verard L. et al., in the article "Fully Automatic Identification of AC and PC landmarks on Brain MRI using scene analysis", IEE Trans MI, 16(5), 610:616, 1997, describe a method for automatically finding the AC and PC which assumes that high resolution magnetic resonance imaging (MRI) images are available. An automatic algorithm uses the data to estimate the MSP. In a first stage, two easily detectable structures—the corpus callosum (CC) and brain stem (BS)—are identified using intensity-based recognition. From these, a small structure—the superior colliculus (Co)—is detected. The PC is obtained from the resultant locations using template matching. The position of the AC is then found by a further template matching step. This method suffers from a number of disadvantages, one of which is the need for the high resolution images.

SUMMARY OF THE INVENTION

The present invention aims to provide a new and useful method for identification of the AC and/or PC landmarks. In particular, the invention aims to make it possible to provide a fast, accurate, robust and clinically practical algorithm.

A first aspect of the invention proposes, in general terms, that the AC and/or PC landmarks are found by firstly identifying structures in the brain (specifically the fornix and/or brainstem) as groups of pixels in an MRI image which have an intensity in ranges defined by one or more thresholds and which obey predefined geometrical criteria. The thresholds are varied until the predefined geometrical criteria are met. The positions of the AC and PC are then estimated based on the identified structures.

A second aspect of the invention proposes, in general terms, that estimates of the positions of the AC and/or PC landmarks are first found using an midsagittal MRI image, but that these estimates are modified using axial and/or coronal MRI images in planes including, and/or proximate to, the estimated positions of the AC and/or PC landmarks.

A specific expression of the first aspect of the invention is a method of estimating the position of a brain landmark which includes:

(i) defining at least one initial threshold value;

(ii) determining whether a region of a midsagittal radiological image including a brain structure includes a group of pixels having intensity values in a range defined by the initial threshold value and which obey one or more predefined geometrical criteria describing the structure;

(iii) if not, then at least once modifying the threshold value and performing step (ii) again;

(iv) if so, identifying the group of identified pixels as the structure; and (v) generating a first estimate of the position of the landmark as a point on the identified structure.

A second expression of the invention is a method of estimating the position of the AC and/or PC landmarks which includes:

(a) using a midsagittal radiological image to estimate the position of the AC and/or PC landmarks in the midsagittal plane;

(b) using the estimated position of the AC and/or PC landmarks to generate one or more axial and/or coronal MRI images, including at least one image including the estimated position of the AC and/or PC landmarks; and (c) analysing the axial and/or coronal MRI images to improve the estimate of the position of the AC and/or PC landmarks.

Either, or both, of the methods may be supplemented by a step of generating a sub-image from the midsagittal MRI image including the first estimated position of the AC landmark or PC landmark, and identifying an improved estimate of the position of the AC landmark or PC landmark from the intensity values in that sub-image.

The two aspects of the invention are independent, but may be freely combined, as discussed below.

In the following detailed description of examples of the invention the term AC landmark and PC landmark are for conciseness referred to simply as the AC and PC respectively.

BRIEF DESCRIPTION OF THE FIGURES

Preferred features of the invention will now be described, for the sake of illustration only, with reference to the following figures in which.

DETAILED DESCRIPTION OF THE EMBODIMENTS

Steps in a method which is an embodiment of the invention are now described. The starting point of the method is a radiological image such as the MRI image shown in FIG. 1. The MRI image is assumed to be oriented according to the radiological convention i.e. with the subject's nose pointing left and his or her neck towards bottom of the image.

The MRI image is an MSP image, meaning that it represents data lying in an estimated mid-sagittal plane. The equation of the MSP can be obtained according to any known estimation algorithm, such as the one described in WO 03/60827 (based on PCT/SG02/00006). However, the invention is not limited to this method of obtaining the MSP.

Figure 1:
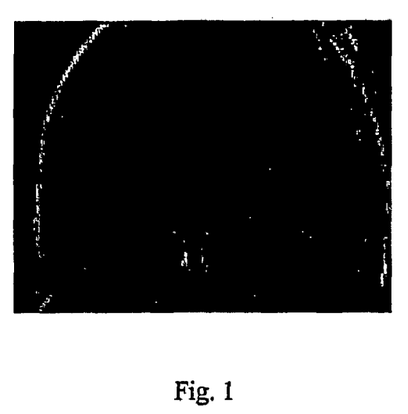
FIG. 1 is the midsagittal MRI image of a brain.
Figure 2:
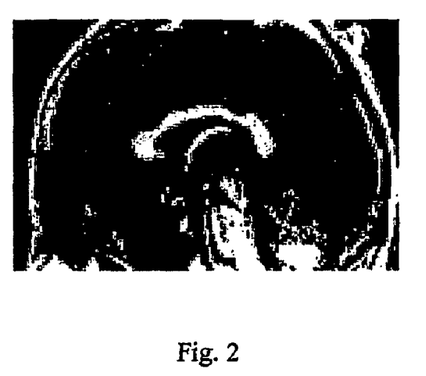
FIG. 2 is a binarised version of FIG. 1.
Figure 3:
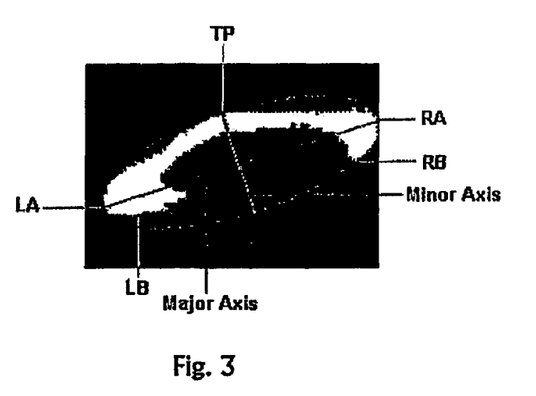
FIG. 3 is an enlarged view of a part of FIG. 2.
Figure 5:
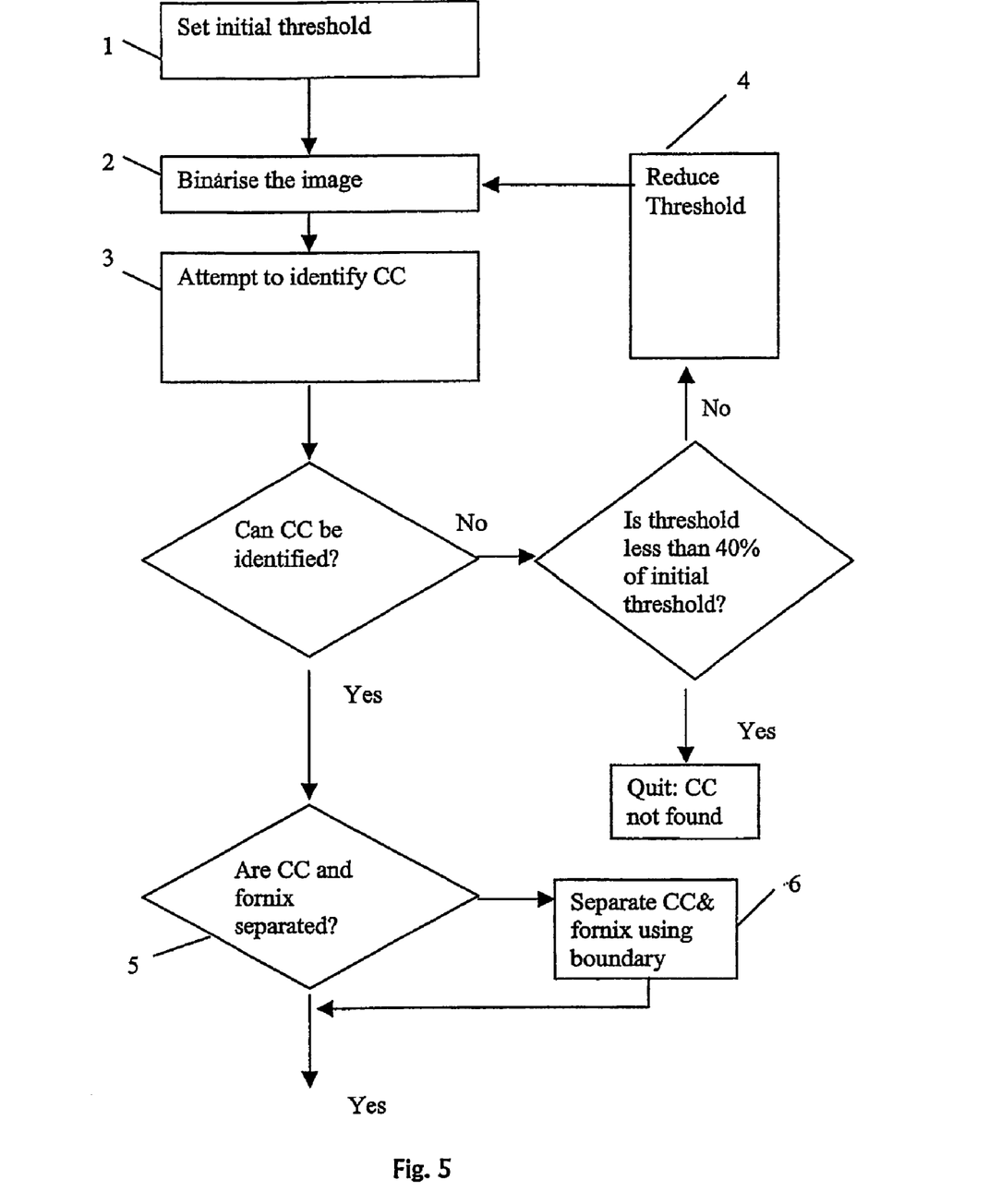
FIG. 5 shows steps of the first part of a method which is an embodiment of the invention.

A first step of the method is to use progressive thresholding to binarise the image. This is illustrated in FIGS. 2 to 3. The method is carried out by the following steps, which are illustrated in FIG. 5:

a) A window of size 11×11 is moved over the entire image of FIG. 1 in an overlapping manner and the mean value of the pixels in the window at every location is recorded.

b) The maximum among the means derived in step (a) recorded is computed.

c) An initial threshold is fixed as 80% of the maximum mean (step 1 in FIG. 5).

d) A binary image is derived from FIG. 1 in which each pixel above the initial threshold is set to white, and each pixel below the threshold is set to black (this is step 2 in FIG. 5, and the result is shown in FIG. 2).

In the binary image, an attempt is made (step 3) to identify the Corpus Callosum (CC) as the structure having the following properties (based on the observations and validation of data):

a) The length of the CC (from the genu to the splenium, i.e. along the major axis) is about 7 to 9 cm.

b) The width of the CC (from the superior point of body or trunk to the inferior point of the genu, i.e. the minor axis) is about 2 to 4 cm.

c) The orientation of the CC (angle of major axis with respect to horizontal axis) is from 5 to 40 degrees.

d) The area of the CC in the binarised image is about 600 to 1000 mm$^2$.

If such a structure is not identified, then it is determined whether the threshold is less than 40% of the initial value, and if not the threshold is reduced by 10% of its current value (step 4), and steps 2 and 3 are repeated.

Steps 2 to 4 are repeated until the CC is detected or the threshold value is less than 40% of the initial value. If the threshold value is less than 40% of initial value and CC is not found, the program quits, stating that CC is not found.

For example, if the starting image is FIG. 1, then a CC will be identified by this procedure. It is shown in FIG. 3. The major axis is marked (as the line LA-RA), as is the minor axis. The points marked RB and LB are the right bottom and left bottom parts.

Figure 4:
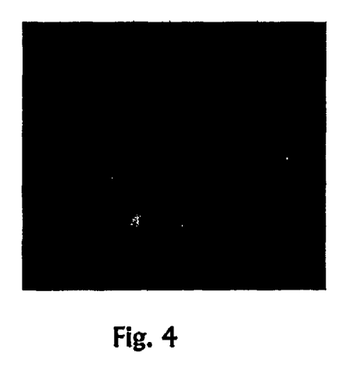
FIG. 4 is an enlarged view of a part of FIG. 1.

More generally, if the CC is found, the method proceeds to step 5 in which a check is carried out to determine whether the CC and fornix are attached:

a) Define a subregion (S1) around CC. FIG. 4 shows this area for the case that the initial MSP image is as in FIG. 1. The height of the sub-region is selected in such a way that the brainstem (BS) and fornix are included. Specifically, the width of the region S1 is selected to be equal to the major axis, and the height was set to 2.5 times the minor axis.

b) For each column in the binary image of S1, the horizontal projection of the columns (i.e. for each row, the sum of the values in that row) is calculated.

Figure 6:
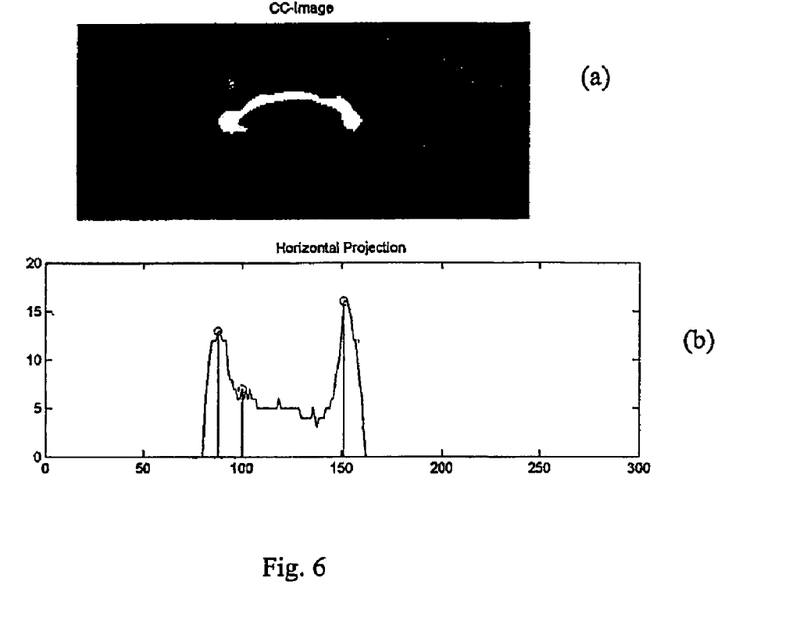
FIG. 6, which is composed of FIGS. 6(*a*) and 6(*b*), shows a binarised version of a first MRI image of the CC, and a horizontal projection of this image.
Figure 7:
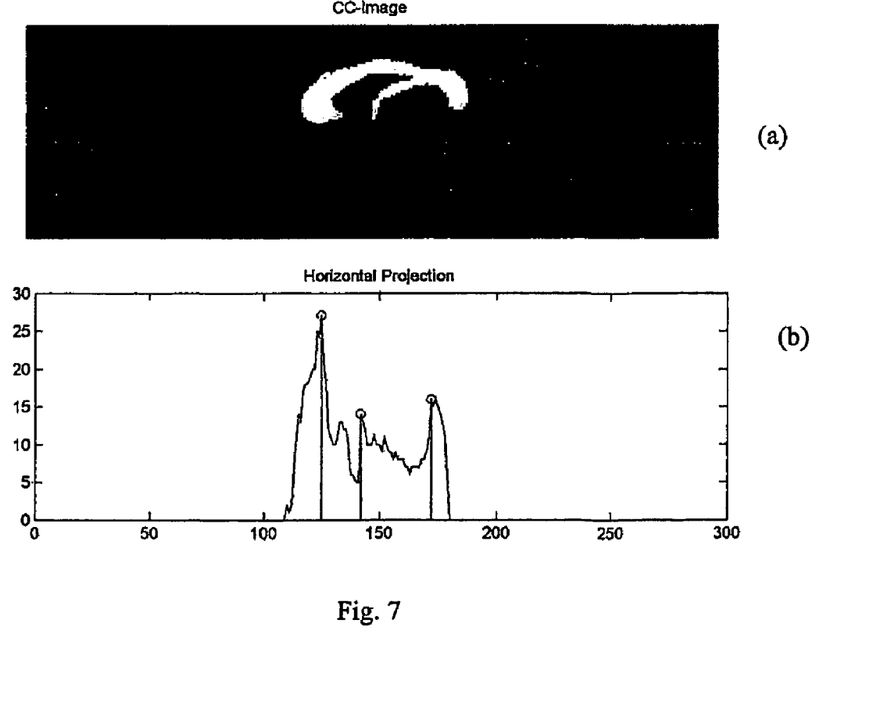
FIG. 7, which is composed of FIGS. 7(*a*) and 7(*b*), shows a binarised version of a second MRI image of the CC, and a horizontal projection of this image.

FIGS. 6 and 7 show two cases. FIGS. 6(a) and 7(a) show the binary image of the region S1 for two different initial MRI images, and FIGS. 6(b) and 7(b) show the corresponding projections.

If there are 3 peaks, or if the centre point of the projection is higher than the mean of the two end points, as in the case of FIG. 7(b), then the fornix and CC are attached together.

Figure 13:
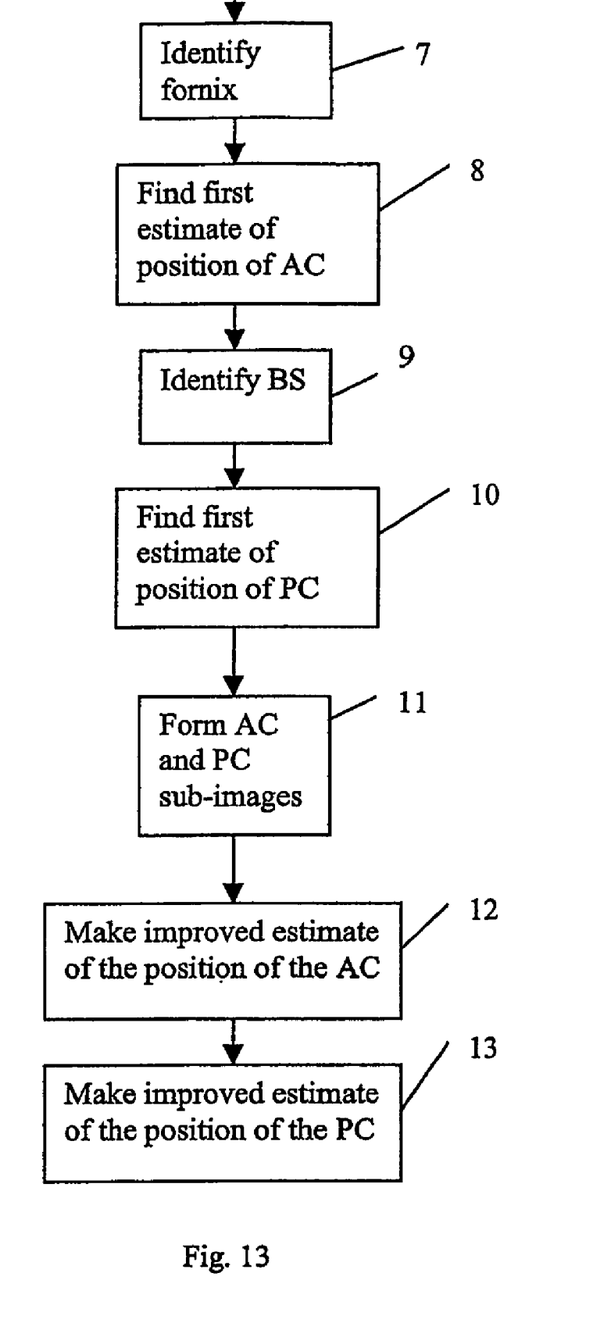
FIG. 13 is steps of a process for improving initial estimates of the positions of the AC and PC in the method which is an embodiment of the invention.

If the fornix is separated from the CC, the method passes to the set of steps shown in FIG. 13. Otherwise, prior to doing this, a step 6 is carried out in which the CC and fornix are separated by boundary tracing and morphological operations.

Figure 8:
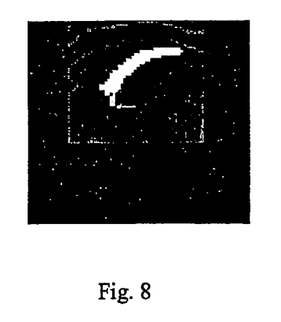
FIG. 8 is a portion of FIG. 1 with the fornix highlighted.

In a first of the steps of FIG. 13 (step 7) the fornix is identified as follows.

a) Within the sub-region S1, a region of interest (ROI) for fornix detection is defined. FIG. 8 shows the sub-region S1, with the parts of S1 which are not within the ROI shown as black. The ROI is defined as the region between 20% and 80% of CC's major axis. The CC structure is subtracted from the ROI.

b) The ROI region is binarised using a progressive thresholding algorithm, resembling the one used above. In this case, pixels are set to white or black according to whether the corresponding value of the MRI image is above or below an initial threshold, and the threshold gradually reduced until a fornix structure can identified in the image. The fornix is identified as a structure in the ROI having the following properties.
i) It is elongated white matter structure
ii) It is located in between the two ends of CC.
iii) It has an orientation >5 degrees & <90 degrees.
iv) It has a major-axis to minor-axis ratio >2.

The entire fornix structure may be not be seen by thresholding, hence to get the complete structure of fornix we do region growing. The intensity values of pixels which are expected to be in the identified fornix structure region are collected and their mean value is computed. From this mean value, two thresholds for region growing of the fornix are calculated. This process involves defining a parameter $M_F$ which is the mean of the pixel intensities in the possible fornix region, and a second parameter $\sigma$ which is the standard deviation of the intensity values in the same region. Then a lower threshold $L_f$ is defined as $M_F-2\sigma$, and an upper threshold $U_f$ is defined as $M_F+2\sigma$. Using these thresholds the full fornix region is obtained by "region growing" as shown in FIG. 8. In this process the pixel values of all regions between the thresholds are assumed to be part of the fornix. The inferior most tip of the fornix is identified as a first estimate of position of the AC (step 8).

Once fornix region, is identified, CC and fornix structures are subtracted from the subregion S1. The result is the region of S1 which is not black in FIG. 9 The brainstem (BS) is identified in this region using anatomical information, that BS is located inferio-posteriorly to CC. The BS is composed of grey and white matter pixels, having higher variance in intensity values than in CC and fornix. Similar to fornix identification, we initially detect the possible BS region using thresholding and perform region growing to extract complete structure. The BS region is characterized by the location of a centroid, intensity variation and width of the region. The lower and upper limits for region growing using 8-neighborhood were calculated as by defining a first parameter MBS which is the mean of the pixel intensities in the possible BS region, and a second parameter $\sigma$ which is the standard deviation of the pixel intensities in the possible BS region $\sigma$. Using these two parameters, we set a lower threshold $L_{BS}$ which is MBS$-3\sigma$, and an upper threshold $U_{BS}$ which is MBS$+2\sigma$. All pixels for which the values of the MRI image are between these thresholds are assumed to be part of the BS. The values of the thresholds given above are proposed based on the composition of grey and white matter pixels in BS. Our observation from the data showed a larger deviation of grey values to the lower side of the mean than to the upper side.

Figure 9:
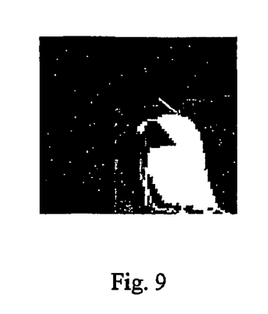
FIG. 9 is a portion of FIG. 1 with the brainstem highlighted.

For the MRI image of FIG. 1, this gives the estimate for the BS as the points shown in white in FIG. 9 (step 9). The upper right most point of BS is defined as our initial estimate of the PC point (step 10).

Figure 10:
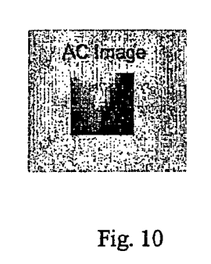
FIG. 10 is a portion of the MRI image including an estimate of the position of the AC.
Figure 11:
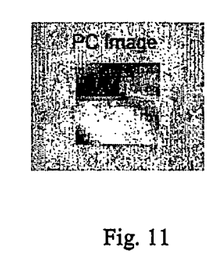
FIG. 11 is a portion of the MRI image including an estimate of the position of the PC.

A next step is to obtain an improved estimate of the positions of the AC and PC. To do this, we generate two sub-images of the initial MRI image (step 11). For the MRI image of FIG. 1, these sub-images are shown in FIGS. 10 and 11 respectively. The sub-images are selected as ROIs respectively around the initial estimates of the positions of the AC and PC. The AC sub-image (FIG. 10) is centered at the initial estimate of the position of the AC, and has a size large enough (e.g. 12×12 mm, which are values which selected based on the observations and anatomy) to include surrounding structures for processing. The construction of PC sub-image is based on variability information that the PC is situated at a distance of 17-42 mm posterior to the AC. The initial estimate of the PC derived above was checked, to see it obeys the above condition, and if so an area large enough (eg. 16×16 mm) to include this point and surrounding structures was defined as PC image. If the condition is not met, the BS region growing is carried out with new thresholds and a re-estimate the initial position of the PC. For all the cases for which we have tested our algorithm, the initial position of the PC obeyed the condition.

The position of the AC is below the inferior tip of fornix, but due to partial volume or imaging artifacts the AC is indistinguishable from the inferior tip of fornix. The AC will usually be manifested as a bright point in the AC image, which can be located by binarising the image and region growing the foreground pixels. An improved estimate of the position of the AC is the inferior-most point of the largest region in the AC sub-image. Around this initial position of the AC we check to see if there are any points with a higher intensity. If such a point is found, it is considered as an improved estimate of the position of the AC. Otherwise, the previous estimate of the AC point itself is retained (step 12).

Figure 12:
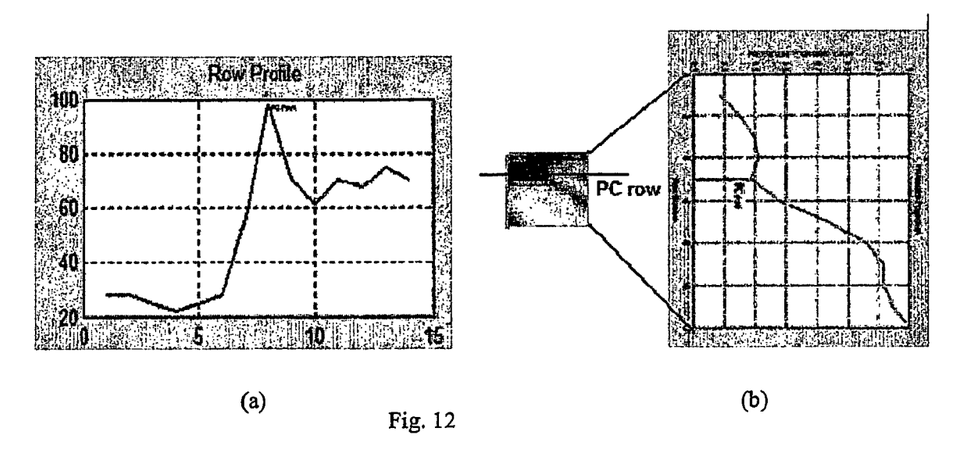
FIG. 12 shows a process carried out on the image of FIG. 11.

An improved estimate of position of the PC is obtained by performing a horizontal projection of the PC image (step 13). In other words, for each row of the PC sub-image we find the respective sum of the corresponding MRI intensities. The resultant plot is shown in FIG. 12(b). The PC image contains a part of the brainstem and the superior colliculus. The point where, the slope changes significantly indicates the row of PC image containing the position of the PC, at least for cases where the superior colliculus is well separated from BS. This row is designated as an initial estimate of the PC row of the PC sub-image. In cases where the superior colliculus is not separated, the slope change is not significant. Hence, two adjacent rows of the identified PC_row, in the PC image are also considered for final refinement. The PC is identified as the point having the maximum change in grey value with the neighbour pixels in the identified PC_row and its adjacent rows. After identifying the PC row, the intensity profile along the rows is taken, as shown in FIG. 12(a), and the column number of the PC in the image is found using FIG. 12(a), as the maximum intensity along the PC row.

The final coordinates of the positions of the AC and PC are mapped back to the volume data using the MSP equation. The corresponding axial slices where the AC and PC are manifested are identified using the MSP equation, voxel size and the volume dimensions.

Figure 14:
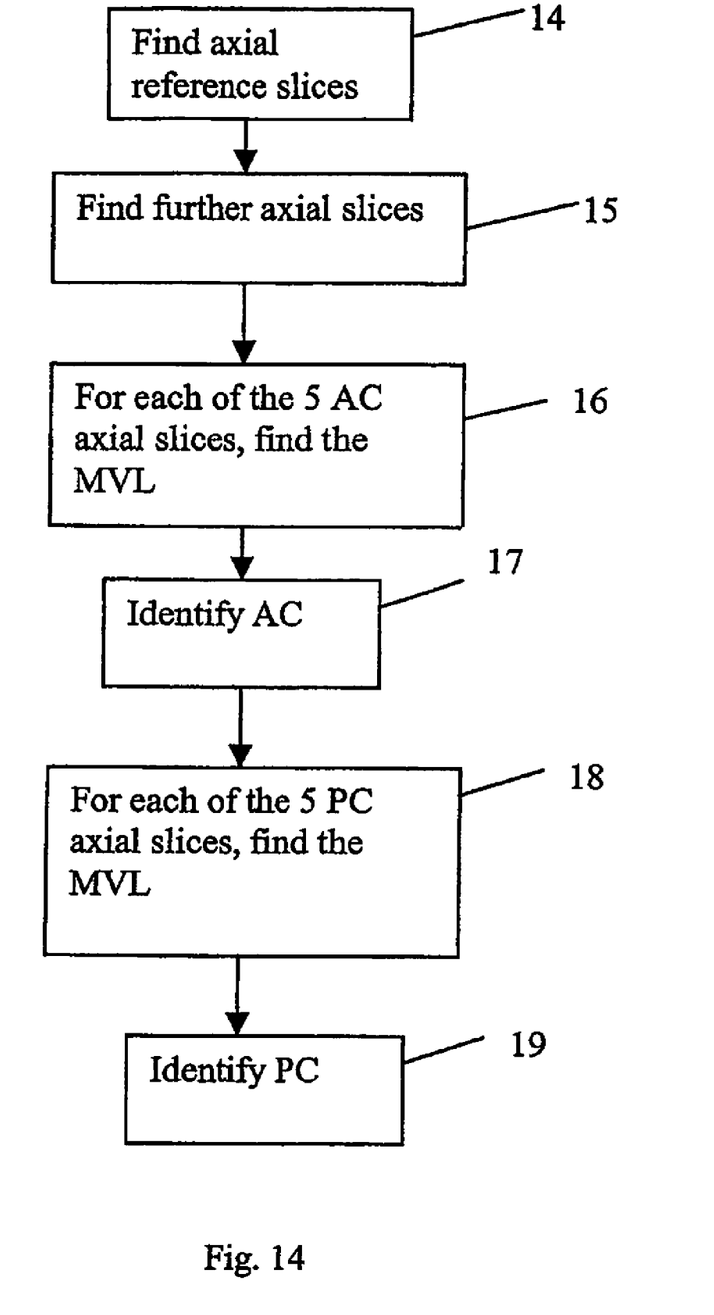
FIG. 14 shows steps of a further process for improving initial estimates of the positions of the AC and PC in the method which is an embodiment of the invention.

FIG. 14 shows the steps of an optional technique for improving the estimates of the estimates of the positions of the AC and PC derived above by processing axial slices.

In a first step (step 14), the axial slices containing the positions of the AC and PC estimated above are found by using the coordinates of the estimated positions of the AC and PC in the midsagittal plane and MSP equation. These two axial slices are termed "reference slices".

Figure 15:
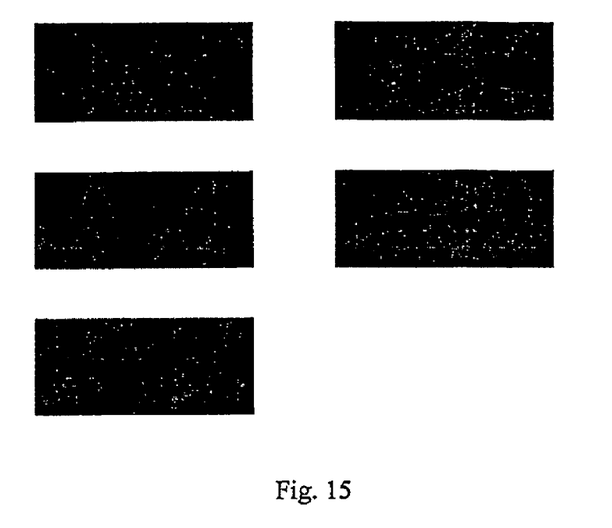
FIG. 15 shows 5 axial MRI images derived using an estimate of the position of the AC.

In a second step (step 15), for each of these AC and PC axial slices, five further slices are defined: two slices above each of the AC and PC axial slices, and two slices below each of the AC and PC axial slices. The resultant five slices derived from the AC reference slice are shown in FIG. 15.

Figure 16:
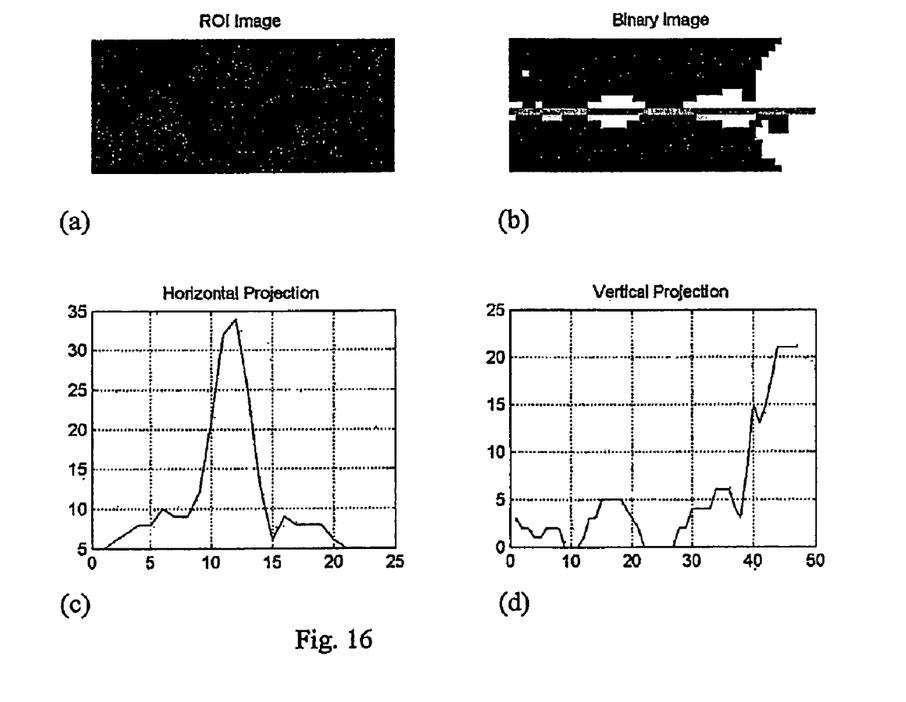
FIG. 16, which is composed of FIG. 16(a) to 16(d), shows a process applied to one of the images of FIG. 15.

In a third step (step 16), for the AC reference slice and each of the four slices derived from it, we form a mean ventricular line (MVL) passing through the third ventricle, by using the horizontal and vertical projections of the corresponding slice. This is shown in FIG. 16, where a slice (shown in FIG. 16(a)) is used to produce a horizontal projection (shown in FIG. 16(c)) and a binary version of the slice (shown in FIG. 16(b)) is used to produce a vertical projection (shown in FIG. 16(d)). The binary version of the slice is produced using a threshold which is selected to be 70% of the region of the mean intensity of the region-of-interest, and pixels below this threshold are shown in FIG. 16(b) as white, and pixels above the threshold as black.

Using the MVL profile, a set of evaluations is performed checking:
1. whether Massa Intermedia is present or the third ventricle is complete, and
2. whether there is a cistern before the AC or the slice has gray matter.

To evaluate the first condition, check along the MVL for continuity of white pixels in the binary image. If the continuity or the length of white pixels is at least 85% of the distance between AC and PC then there is no Massa Intermedia present. If the continuity is broken then Massa Intermedia is present. The distance between the AC and PC is found by the initial estimates of the positions of the AC and PC. The second condition is evaluated by checking the MVL profile before an initial position of the AC. If there are CSF intensity pixels, it is assumed that a cistern is present; else if the pixel intensity is of gray matter then a gray matter is present. These conditions are necessary to decide on what will be the nature of a profile along the MVL and it is used as a reference while searching for the AC and PC.

Figure 17:
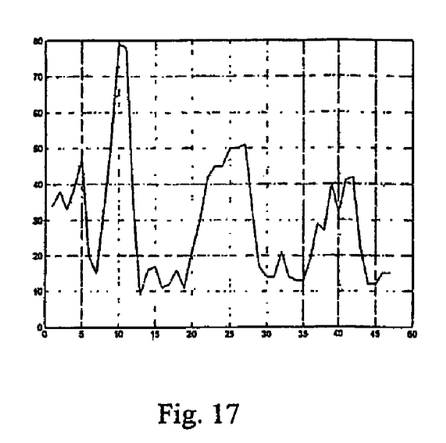
FIG. 17 shows a further step of a process using the images of FIG. 15.

In a fourth step, we examine the profile plot of image values along the MVL (shown in FIG. 17). That is, starting from the midpoint of the profile (i.e. a point in the third ventricle or on the Massa Intermedia) we move leftwards to locate a WM (white matter) peak. This peak is the one end point of the AC. Following the peak, we use the second derivative of the profile to identify the starting point of the AC. Similarly we find the start and end points in all the 5 other slices considered for processing. The AC is assumed to have a width of about 3 mm. Using, these starting and end points and the value of intensity in between these points, region growing is carried out to extract the complete structure of AC (step 17).

Figure 18:
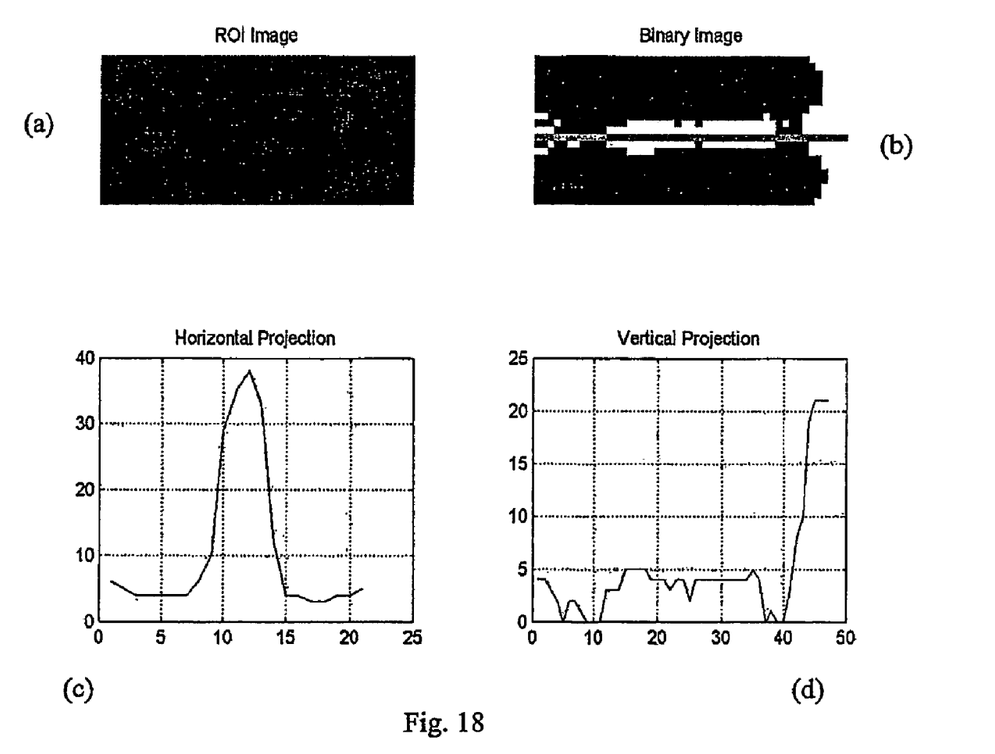
FIG. 18 which is composed of FIG. 18 (a) to FIG. 18(d), shows a process applied to one of the PC axial images (of the 5 slices) obtained using initial estimate of the position of the PC.
Figure 19:
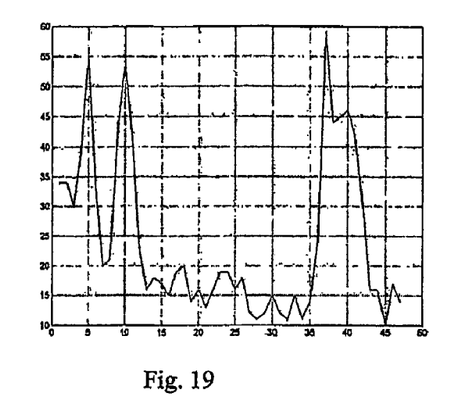
FIG. 19 shows a further step of a process using the images of FIG. 15.

To form an improved estimate of the position of the PC (step 18), we use the MVL profile plot for the PC reference slice, and the four axial slices around the PC reference slice. This is shown, for one of those five axial slices, in FIG. 18. FIG. 18(a) shows one of the axial slices, FIG. 18(c) shows a horizontal projection of it (i.e. summing the values in respective rows), FIG. 18(b) shows a binarised version of it (produced in the same way as FIG. 16(b) described above), and FIG. 18(d) shows a vertical projection of the binarised version (i.e. summing the values in respective columns). This is performed in the same manner as how the MVL is obtained for AC slices. FIG. 19 shows the intensity profile along the MVL. Starting from the middle of the profile and moving towards the right side of the plot, we trace the PC. Since the third ventricle has a cerebro spinal fluid (CSF) which manifests itself as dark matter, the WM peak is identified as the PC location. As in AC identification, the PC too is identified using region growing, as a structure which is cylindrical in shape and having radius of about 1 mm.

Figure 20:
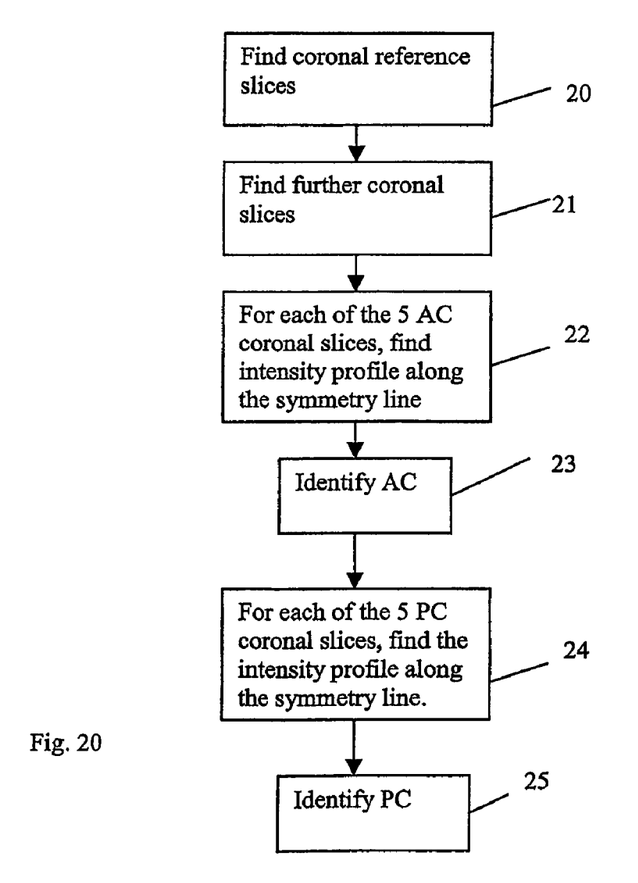
FIG. 20 shows steps of a further process for improving initial estimates of the positions of the AC and PC in the method which is an embodiment of the invention.

FIG. 20 shows the steps of a corresponding technique for improving the estimates of the positions of the AC and PC derived above by processing coronal slices.

From the coordinates of the structures (AC & PC) the corresponding coronal reference slices are identified (step 20).

For each of the AC and PC coronal reference slices, two further slices in the anterior direction and two further slices in the posterior direction are defined.

Figure 21:
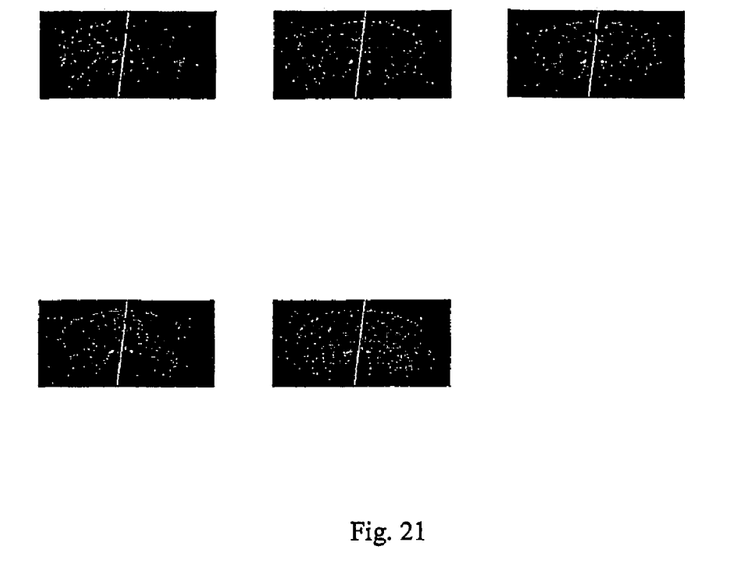
FIG. 21 shows 5 coronal MRI images derived using an estimate of the position of the AC.
Figure 22:
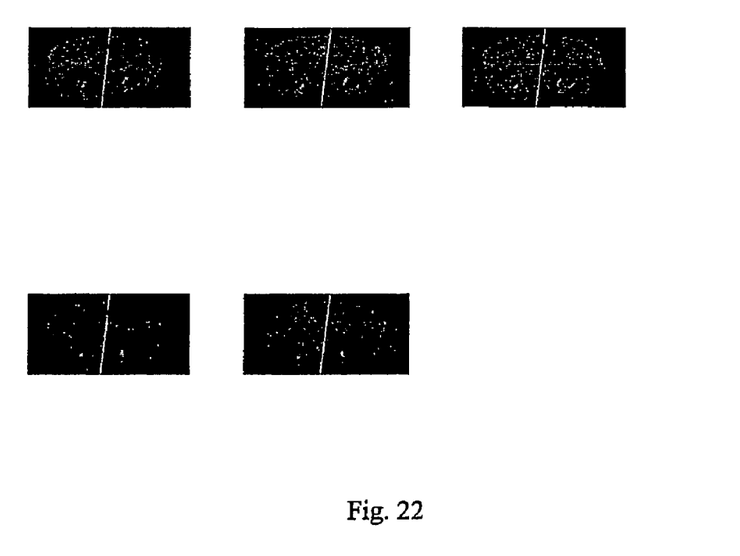
FIG. 22 shows 5 coronal MRI images derived using an estimate of the position of the PC.

Thus, there are a total of 5 slices for the AC, and 5 slices for PC (step 21). The five slices for the AC are shown in FIG. 21, and the five slices for the PC are shown in FIG. 22.

Figure 23:
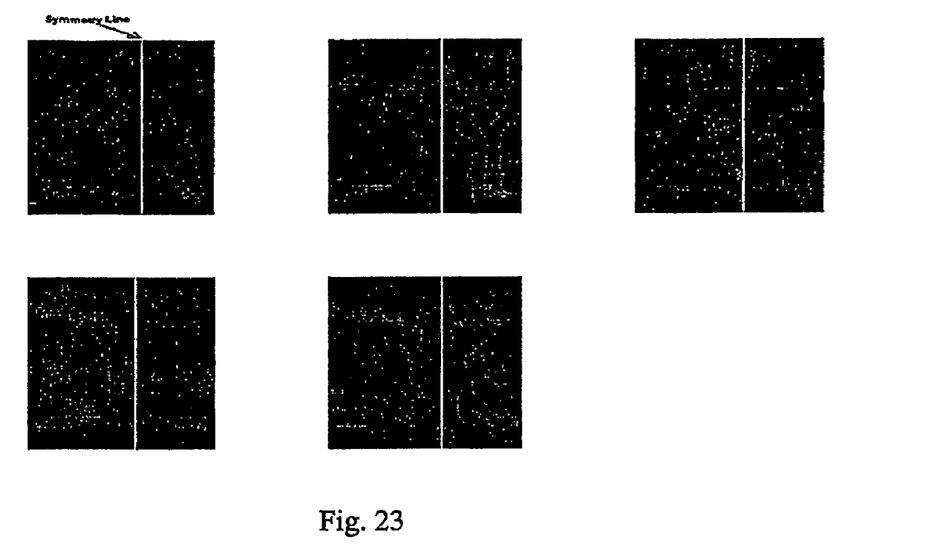
FIG. 23 shows a symmetry line imposed on a part of the images of FIG. 21.

For all the five slices selected a region of interest is selected, consisting of CC, lateral ventricle and AC is selected using the MSP equation. A binarised version of each slice is formed, and the binarised ROIs are used to locate the symmetrical line This is the white line on FIG. 23. The AC and PC are assumed to be on this symmetrical line.

Using the intensity information of CC, a rough estimate of intensity of the AC is obtained as both CC and AC are white matter structures and CC is more homogeneous structure.

Figure 24:
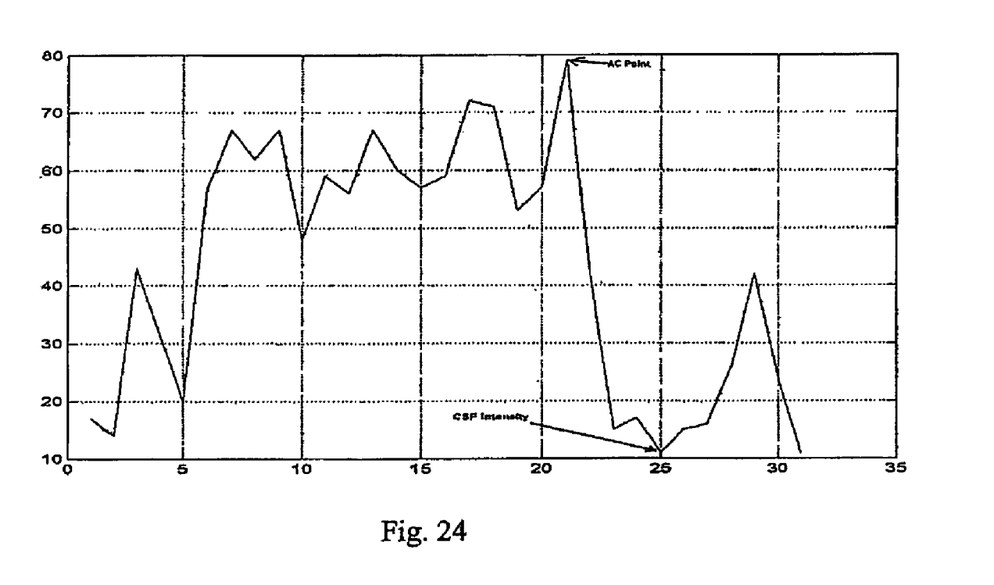
FIG. 24 shows intensity values along a symmetry line shown in FIG. 23.

The intensity value along the symmetry line (shown in FIG. 24) is scanned (step 22) to obtain a white matter peak in the opposite direction of CC. This point is considered as a good estimate for the position of the AC if it has intensity close to white matter intensity and third ventricle can be identified after the AC (low gray value due to CSF).

The further slices around AC reference slice are checked for the above condition. The slices which meet the above conditions are considered to have the AC and from this the radius of the AC is found out (step 23).

Figure 25:
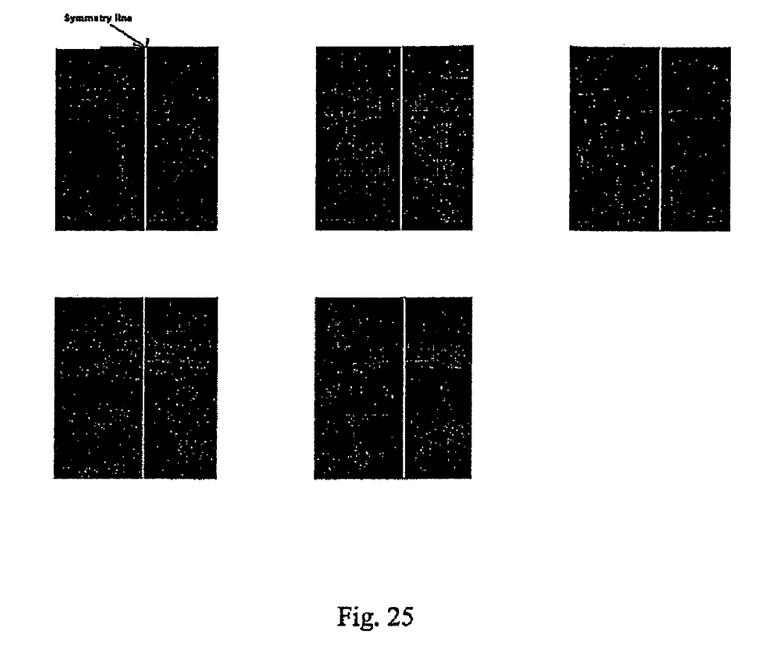
FIG. 25 shows a symmetry line imposed on a part of the images of FIG. 22.
Figure 26:
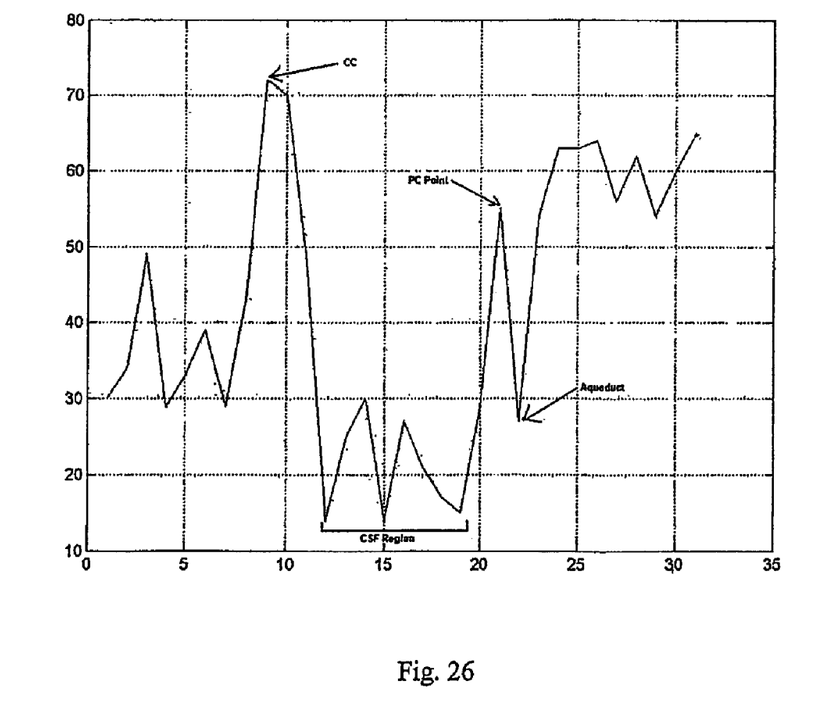
FIG. 26 shows intensity values along a symmetry line shown in FIG. 25.

From the PC slices, the ROI around the MSP line is extracted to find the symmetrical line passing through the ROI (the white line on FIG. 25). The PC is assumed to be on the symmetry line. The location of the CC is known from earlier processing, and hence can be used as a reference to locate white matter structures. The symmetry line (shown in FIG. 26) is scanned (step 24) to locate the CC and find its intensity value. The intensity value of CC is used as a reference to locate the PC as follows.

A scan is done along the symmetry line away from CC position. The CSF region separates the CC and PC. Hence the intensity values will be low in this region. After the CSF region, a small region of pixels of white matter and gray matter mix can be located. After this point, a few pixels of low intensity corresponding to CSF are located which represents the aqueduct. The PC is the region between the CSF matter and the aqueduct.

The above conditions are checked in the PC coronal slices considered for processing. The slices which satisfy the conditions are marked as possessing PC. From the number of slices having the PC the dimensions of the PC structure is found out (step 25).

The final positions of the AC and PC are found using the information obtained from all the three orientations. This is the best position estimate found above in each of the three directions.

Using the final positions of AC and PC, 3 D extraction of the AC and PC is carried out. The PC is assumed to be cylindrical with diameter of about 2 mm. The AC is assumed to be a bent cylinder with diameter about 3 mm. This is based on anatomical knowledge. Primarily we are interested in determining the width of the AC and PC, rather than their height (i.e. length in axial slices).

Although only a single embodiment of the invention has been described in detail, many variations are possible within the scope of the invention as will be clear to a skilled reader.

The invention claimed is:

1. A method of estimating the position of the AC or PC landmarks which includes:
 (a) using a midsagittal radiological image to estimate the position of the AC or PC landmarks in the midsagittal plane;
 (b) using the estimated position of the AC or PC landmarks to generate a plurality of radiological images relating to different slices, including a first image of a slice including the estimated position of the AC or PC landmark and second images of neighboring slices; and (c) analysing the radiological images to improve the estimate of the position of the AC or PC landmarks;

wherein the plurality of generated radiological images are axial images relating to different axial slices including a first axial image of an axial slice containing the estimates of the position of the AC or PC landmark, and second axial images of neighboring axial slices and the method further includes:

using the estimated position of the AC or PC landmark obtained from the midsagittal radiological image to generate a plurality of coronal images relating to different coronal slices, including a first coronal image of a coronal slice including the estimated position of the AC or PC landmark and second coronal images of neighboring coronal slices, the neighboring coronal slices in the second coronal images being in the same orientation as the coronal slice in the first coronal image;

analysing the coronal images to improve the estimate of the position of the AC or PC landmark obtained from the midsagittal radiological image; and further improving the estimate of the position of the AC or PC landmark using the improved estimates of the position of the AC or PC landmark obtained from analysing the axial images and the coronal images.

2. A method according to claim 1 in which step (c) includes deriving a mean ventricular line (MVL), and determining the position of the AC or PC landmarks by scanning intensity values along the MVL.

3. A method according to claim 2 in which the method further includes the steps of determining dimensions of the AC or PC landmarks using the second axial images.

4. A method according to claim 1 in which the step of analysing the coronal images to improve the estimate of the position of the AC or PC landmark obtained from the midsagittal radiological image further includes deriving a symmetry line within the first coronal image including estimates of the position of the AC or PC landmarks, and determining the position of the landmark by scanning intensity values along the symmetry line.

5. A method according to claim 4 in which the method further includes the step of determining dimensions of the AC or PC landmarks using the second coronal images.

6. A method according to claim 1 in which the landmark is the AC.

7. A method according to claim 1 in which the landmark is the PC.

8. A method according to claim 1 in which step (a) is performed by a method of estimating the position of a brain landmark which includes:

(i) defining at least one initial threshold value;

(ii) determining whether a region of a midsagittal radiological image including a brain structure includes a group of pixels having intensity values in a range defined by the initial threshold value and which obey one or more predefined geometrical criteria describing the structure;

(iii) if not, then at least once modifying the threshold value and performing step (ii) again;

(iv) if so, identifying the group of identified pixels as the structure; and (v) generating a first estimate of the position of the landmark as a point on the identified structure wherein the structure is the fornix, and the landmark is the anterior commissure (AC).

9. A non-transitory computer-readable medium storing a computer program product including program instructions which are readable by a computer and cause the computer to perform a method as defined by claim 1.

* * * * *